(12) United States Patent
Lauria et al.

(10) Patent No.: US 8,313,799 B2
(45) Date of Patent: Nov. 20, 2012

(54) ADHESIVE DETECTION METHODS

(75) Inventors: Vincent A. Lauria, Flowery Branch, GA (US); Jason Gillen, Anna, TX (US); Ron McKinley, Lewisville, TX (US)

(73) Assignee: Henkel Corporation, Rocky Hill, CT (US)

( * ) Notice: Subject to any disclaimer, the term of this patent is extended or adjusted under 35 U.S.C. 154(b) by 157 days.

(21) Appl. No.: 12/627,248

(22) Filed: Nov. 30, 2009
(Under 37 CFR 1.47)

(65) Prior Publication Data
US 2010/0304008 A1    Dec. 2, 2010

Related U.S. Application Data

(63) Continuation of application No. PCT/US2008/006132, filed on May 14, 2008.

(60) Provisional application No. 60/940,530, filed on May 29, 2007.

(51) Int. Cl.
*B05D 5/10* (2006.01)

(52) U.S. Cl. ... 427/207.1; 427/8; 427/208.6; 427/208.8; 250/458.1; 250/459.1; 250/461.1; 356/317; 356/318; 356/417

(58) Field of Classification Search ........... 427/8, 207.1, 427/208.6, 208.8; 250/458.1, 459.1, 461.1; 356/317, 318, 417
See application file for complete search history.

(56) References Cited

U.S. PATENT DOCUMENTS

| | | | |
|---|---|---|---|
| 2,588,543 A | 3/1952 | Kunze et al. | |
| 2,595,952 A | 5/1952 | Kunze et al. | |
| 3,778,399 A | 12/1973 | Fazioli et al. | |
| 4,396,739 A | 8/1983 | Sirota et al. | |
| 4,678,824 A | 7/1987 | Lauria | |
| 4,852,795 A * | 8/1989 | Volk, Jr. | 229/92 |
| 5,030,833 A | 7/1991 | Nozaka et al. | |
| 5,208,064 A | 5/1993 | Becker et al. | |
| 5,326,634 A * | 7/1994 | Sato et al. | 428/314.4 |
| 5,380,366 A | 1/1995 | Becker et al. | |
| 5,571,860 A | 11/1996 | Kukkala et al. | |
| 5,648,143 A | 7/1997 | Mehta et al. | |
| 5,663,565 A | 9/1997 | Taylor | |
| 5,939,505 A | 8/1999 | Kukkala | |
| 6,001,910 A | 12/1999 | Blumenthal et al. | |
| 6,086,795 A | 7/2000 | Hatton | |
| 6,103,388 A | 8/2000 | Babcock et al. | |
| 6,138,913 A * | 10/2000 | Cyr et al. | 235/468 |
| 6,281,500 B1 | 8/2001 | Gaon | |
| 6,495,628 B1 * | 12/2002 | Origuchi et al. | 524/803 |
| 6,667,352 B1 | 12/2003 | Kusters et al. | |
| 6,716,941 B2 | 4/2004 | Kerr et al. | |
| 6,761,969 B2 | 7/2004 | Li et al. | |
| 6,802,214 B2 | 10/2004 | Kebart et al. | |
| 6,864,489 B2 | 3/2005 | Chen et al. | |
| 6,972,147 B1 * | 12/2005 | Wei et al. | 428/141 |
| 7,005,176 B2 | 2/2006 | Tojo et al. | |
| 7,239,380 B2 | 7/2007 | Wild et al. | |
| 2004/0528486 | 4/2004 | Heidenfelder et al. | |
| 2004/0167255 A1 * | 8/2004 | Lee et al. | 524/100 |
| 2006/0107732 A1 | 5/2006 | Frank | |

FOREIGN PATENT DOCUMENTS

| | | |
|---|---|---|
| AU | 726971 B2 | 4/1998 |
| EP | 0930350 A1 | 7/1999 |
| JP | 62149775 A | 7/1987 |
| JP | 36417 U | 3/1991 |
| JP | 10309882 A | 11/1998 |
| JP | 1121539 A | 1/1999 |
| JP | 200259940 A | 2/2002 |
| KR | 20060003624 | 1/2006 |

OTHER PUBLICATIONS

"Discover Our World of Effects for Specialty Polymers and Products" Ciba Specialty Chemicals, 2003.
Hunger, Klaus et al. "Pigments, Organic" Ullmann's Encyclopedia of Industrial Chemistry, Wiley-VCH Verlag GmbH & Co. KGaA, 2002.
Schwander, Hansrudolf et al. "Fluorescent Dyes," Wiley-VCH Verlag GmbH & Co. KGaA, 2005, pp. 1-14.

* cited by examiner

*Primary Examiner* — Michael Cleveland
*Assistant Examiner* — Xiao Zhao
(74) *Attorney, Agent, or Firm* — Sun Hee Lehmann

(57) ABSTRACT

Adhesive compositions useful for bonding fluorescent material-containing cellulosic substrates such as envelopes may be formulated using an adhesive polymer such as an emulsion of polyvinyl acetate in water and one or more compounds capable of reducing the degree of fluorescence exhibited by the substrate in areas of the substrate surface having the adhesive coated thereon. When irradiated by short wavelength light, the surface areas containing the adhesive coating appear darker than the surface areas that are free of adhesive, allowing quality control problems associated with application of the adhesive to be readily monitored and corrected. At the same time, however, the adhesive may be formulated such that the fluorescence-reducing compound does not alter the appearance of the adhesive coating when viewed under normal daylight conditions.

7 Claims, No Drawings

ADHESIVE DETECTION METHODS

CROSS-REFERENCE TO RELATED APPLICATIONS

This application is a continuation of International Application No. PCT/US2008/006132 filed May 14, 2008, which claims the benefit of U.S. Provisional Application No. 60/940,530 filed May 29, 2007, the contents of both of which are incorporated herein by reference.

FIELD OF THE INVENTION

The invention relates to methods for detecting where an adhesive coating has been applied to a substrate surface as well as to adhesives useful in the practice of such methods. These methods and adhesives are particularly useful in connection with the bonding of cellulosic substrates such as paper envelopes.

DISCUSSION OF THE RELATED ART

Adhesives based on emulsions of various adhesive polymers have been known for many years and are commonly employed for paper bonding purposes. For example, polyvinyl acetate adhesives are used in bookbinding, carton sealing, boxboard manufacture, bag seaming, tube winding, cup adhesives, remoistenable adhesives on labels, stamps and envelopes, and for bonding various films to cellulosic materials.

To assist in the controlled application of such adhesives to substrate surfaces, it is known to incorporate a fluorescent compound into the adhesive. A fluorescent compound is a substance that emits light in the visible wavelength range when irradiated with short-wavelength ultraviolet light. Ideally, the adhesive containing a fluorescent compound is colorless or nearly colorless under normal (daylight) lighting conditions when applied in a layer or coating to the surface of a white or colorless substrate. That is, a human observer will not be able to readily see the adhesive layer when such layer is exposed to visible light. However, when the adhesive layer is irradiated with short wavelength ultraviolet light, the compound fluoresces and produces a color (e.g., yellow, green, blue) which the human observer can readily detect since it will contrast with the white or colorless substrate. For example, envelope manufacturers may use an adhesive containing a fluorescent compound so that they may easily monitor the quality of the gumline produced when the adhesive is applied to the envelope during construction of the envelope. If, for example, a portion of the applied adhesive extends out beyond the desired region of overlap (where one portion of the envelope is adhered to another portion of the envelope, such as when the envelope stock is folded to form the envelope), this may be easily visualized by exposing the envelope to short wavelength light and checking for any regions that are brighter in appearance (i.e., exhibit a higher degree of fluorescence) attributable to adhesive containing the fluorescent compound.

However, in recent years there has been a trend towards the use of paper stock that itself exhibits some fluorescence (particularly envelope stock that fluoresces with a blue color) when irradiated with short wavelength light. Fluorescent whitening agents, for example, work by emitting bluish light upon excitation in the long ultraviolet region (about 350-400 nm). This emitted light can compensate for the yellowness inherent to certain paper products. In order for the adhesive used in combination with such paper stock to be more readily detected, the concentration of fluorescent compound in the adhesive has been significantly increased. However, this has resulted in problems with the adhesive being visible through the paper stock when the adhesive is used to secure one portion of the stock to another. That is, the adhesive composition has greater color intensity when viewed by visible light as compared to adhesives having lower levels of the fluorescent compound. The adhesive layer that is positioned between two layers of the paper stock and which adheres the paper stock layers together thus exhibits "bleed through", i.e., the color of the adhesive layer under ambient lighting conditions tends to show through the paper stock layers, particularly where such paper stock layers are relatively thin. Additionally, any adhesive which is applied (e.g., inadvertently) to the substrate surface in an area other than the area of overlap between the two layers of paper stock will also exhibit an objectionable visible color intensity. The perceived quality of the assembled article (e.g., envelope) is thereby adversely affected, since the manufacturer as well as the end consumer would greatly prefer a product that does not exhibit such visible coloration under normal use conditions.

It would therefore be desirable to develop alternative methods for visualizing where an adhesive has been applied to a fluorescent substrate surface that avoid the incorporation of fluorescent compounds in the adhesive and do not adversely affect the performance of the adhesive or the appearance of the applied adhesive coating under daylight lighting conditions.

SUMMARY OF THE INVENTION

The present invention provides a method for detecting the presence of an adhesive coating on a substrate surface that fluoresces when exposed to ultraviolet light, said method comprising:

a) applying an adhesive to said substrate surface to form a coating of said adhesive on at least one portion of said substrate surface; and b) observing said substrate surface having the coating thereon while exposing said substrate surface to a source of ultraviolet radiation; wherein said adhesive is provided with at least one compound effective to reduce the intensity of the fluorescence emitted by said substrate in said at least one portion of the substrate surface having said coating thereon.

The invention further provides a method of detecting coverage of an adhesive on a substrate, said method comprising:

a) selecting a substrate comprising at least one fluorescent compound;

b) coating a surface of said substrate with an adhesive comprising at least one adhesive polymer and at least one ultraviolet light absorber;

c) exposing said surface of said substrate coated with said adhesive to ultraviolet radiation capable of exciting said at least one fluorescent compound; and d) detecting the presence, absence or intensity of fluorescence across said surface to determine the extent of surface coverage by said adhesive.

The decreased fluorescence in the portions of the substrate surface where the adhesive coating has been applied permits an observer to readily determine whether the adhesive is present in only the desired areas of the substrate surface and whether any corrective action needs to be taken.

DETAILED DESCRIPTION OF CERTAIN EMBODIMENTS OF THE INVENTION

Although the methods described herein could be employed with any of the known types of adhesives including hot melt adhesives, solvent-based adhesives, reactive adhesives, radiation curable adhesives, thermally curable adhesives, contact adhesives, pressure sensitive adhesives, one-component adhesives, and two-component adhesives, in especially preferred embodiments of the invention the adhesive is water-based. In particular, such adhesives may comprise an emulsion in water of one or more adhesive polymers, a solution in water of one or more adhesive polymers, or an aqueous mixture containing both solubilized adhesive polymer(s) and emulsified adhesive polymer(s).

Adhesive polymers suitable for use in the present invention include any of the water-insoluble polymeric substances known in the adhesive art which are capable of being dispersed in an aqueous medium to form a stable emulsion of finely divided particles that, when applied to a substrate surface, set by the release of water (i.e., drying) to provide a film of the polymer particles (which typically coalesce when dry). The polymer film creates an adhesive bond between the substrate surface and a second substrate surface that has been brought into contact with the applied adhesive coating. The polymer thus may be any of the resinous, thermoplastic, thermoset, or rubbery (elastomeric) substances conventionally used in water-based adhesives. Synthetic as well as natural polymers (e.g., polysaccharides) are suitable for use.

Emulsions of vinyl ester homopolymers and/or copolymers are especially useful in the adhesives of the present invention. The vinyl ester monomer(s) utilized in the preparation of such homopolymer or copolymer may be an ester of an alkanoic acid containing from one to about 12 carbon atoms. Typical examples include, but are not limited to, vinyl formate, vinyl acetate, vinyl propionate, vinyl butyrate, vinyl isobutyrate, vinyl valerate, vinyl 2-ethyl-hexanoate, vinyl isoctanoate, vinyl nonoate, vinyl decanoate, vinyl pivalate, vinyl versatate, and the like, including vinyl esters of longer chain fatty acids. Of these, vinyl acetate is generally preferred because of its ready availability and low cost.

The vinyl ester monomer may be homopolymerized or copolymerized with one or more monomers other than a vinyl ester monomer. Suitable comonomers include, for instance, alpha olefins such as ethylene, ethylenically unsaturated monocarboxylic acids such as acrylic acid, itaconic, citraconic and crotonic acids, nitriles of ethylenically unsaturated monocarboxylic acids such as acrylonitrile, ethylenically unsaturated dicarboxylic acids such as maleic and fumaric acids, anhydrides of ethylenically unsaturated dicarboxylic acids such as maleic anhydride, and $C_1$-$C_9$ esters of mono- and dicarboxylic acids containing at least one carbon-carbon double bond such as acrylic acid, methacrylic acid, fumaric acid and maleic acid. Examples of suitable comonomers of the latter type include 2-ethyl hexyl acrylate and dibutyl maleate. N-methylol comonomers such as N-methylolacrylamide may also be used, as can vinyl monomers such as N-vinyl formamide, N-vinyl pyrrolidone, vinyl chloride, and vinylidene chloride.

Emulsions of both vinyl ester homopolymers and copolymers suitable for use in the present adhesive compositions can be prepared by methods well known in the art. For instance, the polymerization of the aforementioned monomers can be carried out by means of free radical initiated polymerization wherein the monomer(s) is/are heated in the presence of a free radical initiator such as azobisisobutyronitrile or benzoyl peroxide. This polymerization is generally conducted in an aqueous medium, with the monomer(s) being emulsified therein. Emulsifiers and/or protective colloids such as polyvinyl alcohol or hydroxy-alkylated polysaccharides are often utilized. Typically, the emulsion of vinyl acetate polymer thereby obtained will have a solids content of from about 50 to about 80% by weight.

Methods of preparing emulsions in water of vinyl ester homopolymers and copolymers that are suitable for use in adhesive formulations are well known in the art. For example, the emulsion polymerization techniques described in the following U.S. Pat. Nos. (each of which is incorporated herein by reference in its entirety) may be utilized: 2,595,952; 2,588,543; 3,778,399; 4,396,739; 4,575,525; 4,678,824; 5,571,860; 5,939,505; 6,667,352; and 6,716,941.

Suitable vinyl ester homopolymer and copolymer emulsions that may be employed as components of the present invention are also available from commercial sources.

Polyacrylate homopolymers and copolymers as well as styrene copolymers (e.g., styrene/maleic anhydride copolymers) may also be used as the adhesive polymer in the compositions of the present invention. Suitable polyacrylates include polymers and copolymers prepared by polymerization of one or more acrylic monomers such as acrylic acid, methacrylic acid, C1-C12 alkyl esters of acrylic acid, C1-C12 alkyl esters of methacrylic acid, and C1-C8 alkyl-substituted acrylamides and methacrylamides.

The adhesive polymer could also be an emulsion (latex) of a diene polymer or copolymer such as, for example, a styrene-butadiene rubber (SBR), neoprene-butadiene rubber, chloroprene rubber, natural rubber, isoprene rubber, or acrylate-butadiene rubber.

The adhesive polymer may also be a polysaccharide or other naturally occurring polymer such as, for example, a starch or dextrin or chemically modified derivative thereof (e.g., crosslinked or hydrophobically modified starch). Mixtures of a) a polyvinyl alcohol and/or an ethylene vinyl acetate copolymer and b) a starch and/or dextrin are particularly suitable for use as the adhesive polymer component.

The adhesive polymer may optionally contain reactive groups that permit the adhesive to be crosslinked, which may help to improve the water resistance of the adhesive bond formed from the adhesive composition.

Typically, the adhesive polymer emulsion comprises the majority by weight of the adhesive compositions used in the method of the present invention. Although the concentration of the adhesive polymer emulsion is not thought to be especially critical, generally speaking the emulsion will comprise from about 50 to about 90 parts by weight per 100 parts by weight of the adhesive composition as a whole.

The adhesive composition additionally contains one or more compounds effective in reducing the intensity of the fluorescence emitted by the substrate to which the adhesive composition has been applied. Generally speaking, such compounds are absorbers of ultraviolet light and therefore are sometimes referred to herein as "UV light absorbers". Suitable UV light absorbers for purposes of the present invention include benzophenones (e.g., hydroxy-substituted benzophenones), benzotriazoles (e.g., hydroxy-substituted benzotriazoles), triazines (e.g., hydroxy-substituted triazines), benzoxazinones (e.g., non-hydroxy-substituted benzoxazinones), hindered benzoates (e.g., hydroxy-substituted hindered benzoates), p-methoxy benzylidene malonate esters, non-hydroxy-substituted oxanilides and hindered amines. Combinations of different UV light absorbers may be utilized if so desired. In particularly preferred embodiments, the UV light absorber is a substituted o-hydroxybenzophenone, a substituted o-hydroxyphenyl salicylate, and/or a substituted 2-(o-hydroxyphenyl)-benzotriazole. Where the adhesive is a water-based adhesive, it will generally be desirable for the UV light absorber to be soluble in water or to be in the form of fine particles that are dispersed or emulsified in water. Additionally, the UV light absorber is preferably selected such that it does not impart a visible (in daylight) color to the adhesive composition and/or does not adversely affect the properties of the adhesive composition. Suitable UV light absorbers are available from a number of commercial sources including Ciba Specialty Chemicals (under the tradenames "Tinuvin" and "Chimmasorb") and from Cytec Industries (under the tradename "Cyasorb"). An example of an especially preferred UV light absorber is N-(ethoxycarbonylphenyl)-N'-methyl-N'-phenyl formamidine (CAS 57834-33-0; commercially available from Ciba Specialty Chemicals under the tradename "Tinuvin 101").

The amount of UV light absorber that is incorporated into the adhesive composition may vary depending upon the fluorescent activity of the substrate to which the adhesive is to be applied, the thickness of the adhesive coating that is to be formed on the substrate surface, the means by which the fluorescence of the adhesive-coated substrate following irradiation by ultraviolet light is to be viewed or measured, the effectiveness of the UV light absorber in absorbing ultraviolet light, as well as other factors, but generally will be an amount effective to permit the applied adhesive on the substrate surface to be readily detected by a human observer or a fluorescent light intensity measuring device following ultraviolet light irradiation of the adhesive layer. Typically, the UV light absorber is present in an amount ranging from about 0.01 to about 1 weight percent, based on the total weight of the entire adhesive composition.

In preferred embodiments of the invention, the adhesive (when applied as a coating to a substrate surface) is colorless or transparent, or both colorless and transparent, when exposed to visible light (e.g., when observed under daylight conditions). To modify the visual appearance of the adhesive composition, it may be desirable to add one or more clarifiers (clarifying agents). Such optional clarifiers help to make the adhesive composition more transparent or clear (i.e., less opaque), thereby making the adhesive even less visible to a human observer under normal daylight lighting conditions. Suitable clarifiers include, for example, glycol oligomers such as ethylene glycol oligomers (e.g., triethylene glycol, tetraethylene glycol, pentaethylene glycol, and mixtures thereof). In certain embodiments, the adhesive compositions of the present invention may contain up to 5 parts by weight (e.g., 0.5 to 5 parts by weight) clarifier, per 100 parts by weight of the adhesive composition.

In addition to the foregoing constituents, the adhesives used in the present invention may further comprise one or more stabilizers, humectants, tackifiers, fillers, protective colloids (e.g., polyethylene glycol, cellulosics, polyvinyl pyrrolidone), emulsifiers, surfactants, nonreactive diluents (solvents, especially water-soluble solvents, although in preferred embodiments the adhesive is free or essentially free of organic solvents), adhesion promoters, crosslinking agents, defoamers, thickeners, thixotropic agents, plasticizers, antioxidants, preservatives, biocides and the like. Such additional and optional additives may be any of the materials known in the water-based adhesive art. Water may also be added to the adhesive composition (beyond what is already supplied through addition of the water-based emulsion of the adhesive polymer and possibly other water-containing ingredients) in order to achieve the desired viscosity or impart other properties to the adhesive.

A water-soluble polymer such as polyvinyl alcohol and partial hydrolysis products of polyvinyl acetate may be included in the adhesive compositions of the present invention, typically at a level of from 0.1 to 10 parts by weight or 0.5 to 5 parts by weight based on 100 parts by weight of the adhesive composition as a whole.

If desired, one or more of the plasticizers conventionally used in waterborne adhesives may be present in the adhesive composition. Representative plasticizers include phthalate, glycolate, butyrate, 2-ethyl hexoate, and phosphate plasticizers such as acetyl tributyl citrate, butyl benzyl phthalate, butyl phthalyl butyl glycolate, dibutyl phthalate, dibutyl sebacate, diethyl phthalate, diethylene glycol dibenzoate, dipropylene glycol, dipropylene glycol dibenzoate, ethyl phthalyl ethyl glycolate, ethyl-p-toluene sulfonamide, hexylene glycol, methyl phthalyl ethyl glycolate, polyoxyethylene aryl ethers, tributoxy ethyl phthalate, and the triethylene glycol polyesters of benzoic acid and phthalic acid. The plasticizer typically may comprise 2 to 20 parts by weight, for example 3 to 15 parts by weight, per 100 parts by weight of the adhesive composition.

If desired, one or more tackifiers may optionally be incorporated into the adhesive composition, generally at levels up to about 20 parts by weight, e.g., 2 to 10 parts by weight per 100 parts by weight of the total adhesive composition. Representative tackifiers include coumarone-indene, ester gum, gum rosin, hydrocarbon resins, hydrogenated rosin, phenolic modified hydrocarbon resins, rosin esters, tall oil rosins, terpene phenolic resins, terpene resins, toluene-sulfonamide-formaldehyde resin, wood rosins, borax, boric acid, and citric acid.

Useful thickeners include oliginates, bentonite, casein, fumed silica, guar gum, gum tragacanth, hydroxyethylcellulose, locust bean gum, methylcellulose, polyacrylic acid salts (e.g., ammonium, potassium, sodium salts), polyvinyl alcohol, sodium carboxymethyl cellulose, and starches, and if present, are typically employed in amounts up to 5 parts by weight per 100 parts by weight of the adhesive composition in total.

Suitable fillers include bentonite, calcium carbonate, calcium silicate, clay, mica, nut shell flours, silica, talc, uncooked starches, and wood flour, and if present, generally comprise up to 20 parts by weight per 100 parts by weight of the adhesive composition in total.

Humectants suitable for use include calcium chloride, diethylene glycol, glycerine, hexylene glycol, propylene glycol, magnesium chloride, sodium nitrate, sorbitol, sucrose, and urea, and, if present, may comprise up to 20 parts by weight per 100 parts by weight of the adhesive composition.

In certain embodiments, the adhesive may be comprised of the following ingredients (the amounts stated are expressed in parts by weight, based on a total of 100 parts by weight of the adhesive):

|  | Parts |
|---|---|
| Formulation I | |
| Ethylene vinyl acetate copolymer emulsion and/or polyvinyl acetate homopolymer emulsion | 20-99.99 |
| Polyvinyl alcohol solution | 0-20 |
| Plasticizer(s) | 0-20 |
| Humectant(s) | 0-25 |
| Solvent(s) | 0-15 |
| UV light absorber(s) | 0.01-1.0 |
| Defoamer(s) and/or preservative(s) | 0.1-1.5 |
| pH adjustment agent(s) | 0-1 |
| Thickener(s) | 0-3 |
| Additional water | 0-9 |
| Formulation II | |

-continued

|  | Parts |
|---|---|
| Water | 0-20 |
| Starch and/or dextrin | 1-40 |
| Humectant(s) | 0-30 |
| PVA and/or EVA resin emulsion (preferably dextrin-emulsified for compatibility) | 0-99.99 |
| Tackifier(s) | 0-5 |
| UV light absorber(s) | 0.01-1.0 |
| Defoamer(s) and/or preservative(s) | 0.1-1.5 |
| pH adjustment agent(s) | 0-1.0 |
| Additional water | 0-3 |
| Formulation III |  |
| Water-based emulsion(s) of vinyl ester homopolymer(s) or copolymer(s) | 50-90 |
| Polyvinyl alcohol aqueous solution (e.g., 20-60 wt. % solids) | 0-20 |
| Plasticizer(s) | 0-20 |
| Humectant(s) | 0-25 |
| Clarifier(s) | 0.5-5 |
| UV light absorber(s) | 0.01-1 |
| Mineral acid(s) | 0.5-1.5 |
| Defoamer(s) and/or preservative(s) | 0.3-1.5 |
| Additional water | 1-10 |

The adhesive compositions used in the present invention should be formulated so as to have viscosity properties suitable for the desired application. Typically, it will be desirable to adjust the viscosity to be relatively low at the temperature at which the adhesive is to be applied to the substrate so as to facilitate wetting of the substrate surface. When the adhesive composition is utilized in the manufacture of envelopes, for example, the application temperature is typically about 35 to about 45 degrees C. and the viscosity of the adhesive at 25 degrees C. is typically from about 500 cps to about 25,000 cps (e.g., from about 900 cps to about 3000 cps).

Although the adhesive detection methods of this invention are particularly suitable for use in the manufacture of envelopes and packaging paper, they may also be used in a wide variety of other bonding or joining applications such as, for example, packaging and bottle labeling, case and carton forming and sealing, tube winding, bag manufacture, paper and flexible film lamination and the like, with numerous different substrates. Suitable substrates include paper (including printed and/or coated paper), paperboard, cardboard, particle board, wood and other cellulosic substrates as well as textiles, leather, plastic sheets and films, metallized plastic films, glass, rubber, and metal sheets and foils.

As mentioned previously, the substrate to which the adhesive composition is applied should contain one or more fluorescent compounds in an amount effective to cause the surface of the substrate (in the absence of the adhesive composition) to fluoresce when irradiated with ultraviolet light. Such fluorescent compounds, as well as methods for incorporating such compounds into such substrates, are well known in the art and are sometimes referred to as "optical brighteners" or "whitening agents". Suitable fluorescent compounds include dyes and pigments that will absorb radiation in the ultraviolet spectrum and emit light in the visible spectrum, and include, for example, carbocycles (e.g., triazinylaminostilbenes, divinylstilbenes), benzoxazoles, furans, benzo[b]furans, benzimidazoles, 1,3-diphenyl-2-pyrazolines, coumarins, naphthalimides, and 1,3,5-triazin-2-yl derivatives. Daylight fluorescent pigments are especially useful. Any of the conventional methods for combining the fluorescent compound with the substrate may be utilized, such as, for example, coating, dyeing and the like. Where the substrate is paper, for example, the fluorescent compound can be added at various stages of papermaking such as in the pulp, to the paper surface, and/or during application of a coating to the paper surface.

Generally speaking, the adhesive may be applied to the substrate by any conventional coating technique. For example, where the adhesive is water-based, it may be applied using any of the application methods typically used for waterborne adhesives, including mechanical coating, brushing, or spraying. A substrate bearing a layer of the coated adhesive may then be brought into face-to-face contact with a second substrate, which may or may not also have an adhesive layer coated thereon. The adhesive coating may be dried before it is bonded to a second substrate, then remoistened shortly before being contacted with such second substrate. Pressure may be applied to bring the two substrates into firm contact with each other.

When manufacturing envelopes, for example, the adhesive composition can be readily applied to the material comprising the main body of the envelope (typically paper or other cellulosic substrate) in the regions or areas desired by means of any conventional envelope-making apparatus. Typically, the coating weight of the adhesive layer is adjusted to be sufficient to provide a dried adhesive layer of about 0.1 to about 2 mils in thickness.

In general, drying of the adhesive composition is carried out near ambient (room) temperatures, e.g., from about 20 to about 35 degrees C., although drying can be accelerated by applying heat to and/or circulating/blowing air over the adhesive coating or layer.

Either before or after drying of the layer of adhesive composition that has been applied to a substrate surface, the substrate surface may be exposed to radiation capable of exciting one or more fluorescent compounds present in or on the substrate surface and the presence, absence, location or amount of adhesive composition on the substrate surface may be detected, measured or observed by the fluorescence exhibited. That is, the presence, absence and relative intensity of fluorescence provides information about the presence of the adhesive composition on the substrate surface. Where or when the adhesive composition is not present, the substrate surface will fully fluoresce when the fluorescent compounds in or on the substrate surface are excited by appropriate radiation (i.e., radiation that can be absorbed by the fluorescent compound and that causes such material to emit light in the visible spectrum). The presence or absence of fluorescence is visible to a human observer, which allows the observer to determine information about the substrate surface, including the absence of adhesive on the substrate surface, the presence of adhesive on the substrate surface, the positioning of the adhesive on the substrate surface (e.g., whether the adhesive coating has been applied to the desired areas of the substrate surface), the amount of adhesive on the substrate surface, and the evenness of the adhesive coating on the substrate surface. This information can then be used to determine what adjustments may need to be made, such as, for example, changing the manner in which the adhesive is being applied to the substrate surface. In an automated envelope assembly process, for example, observing the gumline under conditions where the fluorescent material in or on the substrate surface is excited by ultraviolet light and caused to emit visible light will inform the observer whether any corrective measures should be made so that the gumline is created only in the desired areas of the paper stock used to form the envelopes. The gumline will generally be visible as a black or darker band against a more highly fluorescent background generated by fluorescence of those areas of the paper or other substrate where adhesive is not present. The fluorescent paper stocks in commercial use currently will typically emit fluorescent light that is bright blue in color when irradiated with ultraviolet light, for example.

The intensity of the fluorescence signal can be used to monitor the amount and/or location of adhesive on the substrate surface. The fluorescence intensity can be viewed by a human observer (either directly or by remote means such as a camera or other monitoring device) or measured using an instrument capable of detecting fluorescence intensity. Examples of such instruments include fluorescence spectrometers and radiometers. Useful sources of radiation for purposes of exciting the fluorescent compound include any source that emits ultraviolet (short wavelength) light such as, for example, black light devices.

The invention claimed is:

1. A method of detecting coverage of an adhesive on a substrate, said method comprising:
   a) selecting a cellulosic substrate comprising at least one fluorescent compound;
   b) coating a surface of said substrate with an adhesive comprising at least one water-based adhesive polymer and at least one ultraviolet light absorber;
   c) exposing said surface of said substrate coated with said adhesive to ultraviolet radiation capable of exciting said at least one fluorescent compound, which has a wavelength of from 200 to 400 nm; and
   d) detecting the presence, absence or intensity of fluorescence across said surface to determine the extent of surface coverage by said adhesive.

2. The method of claim 1, wherein said fluorescent compound emits radiation having a wavelength of from 400 nm to 750 nm.

3. The method of claim 1, wherein said detecting comprises visually observing the presence, absence or intensity of fluorescence.

4. The method of claim 1, wherein said substrate is an envelope.

5. The method of claim 1, wherein said at least one ultraviolet light absorber is selected from the group consisting of benzophenones, benzotriazoles, triazines, benzoxazinones, hindered benzoates, p-methoxy benzylidene malonate esters, non-hydroxy-substituted oxanilides and hindered amines.

6. The method of claim 1, wherein said at least one ultraviolet light absorber is selected from the group consisting of substituted o-hydroxybenzophenones, substituted o-hydroxyphenyl salicylates, and substituted 2-(o-hydroxyphenyl) benzotriazoles.

7. The method of claim 1, wherein said adhesive is comprised of from 0.01 to 1 weight percent of said at least one ultraviolet light absorber.

* * * * *